(12) United States Patent
Mcgregor et al.

(10) Patent No.: US 11,660,378 B2
(45) Date of Patent: May 30, 2023

(54) ENDOSCOPIC RAMAN SPECTROSCOPY DEVICE

(71) Applicant: PROVINCIAL HEALTH SERVICES AUTHORITY, Vancouver (CA)

(72) Inventors: Hanna Claire Mcgregor, Surrey (CA); Michael Short, Coquitlam (CA); Haishan Zeng, Vancouver (CA)

(73) Assignee: Provincial Health Services Authority, Vancouver (CA)

( * ) Notice: Subject to any disclaimer, the term of this patent is extended or adjusted under 35 U.S.C. 154(b) by 165 days.

(21) Appl. No.: 16/958,062

(22) PCT Filed: Jan. 25, 2019

(86) PCT No.: PCT/CA2019/050095
§ 371 (c)(1),
(2) Date: Jun. 25, 2020

(87) PCT Pub. No.: WO2019/144237
PCT Pub. Date: Aug. 1, 2019

(65) Prior Publication Data
US 2021/0059513 A1    Mar. 4, 2021

Related U.S. Application Data

(60) Provisional application No. 62/621,666, filed on Jan. 25, 2018.

(51) Int. Cl.
*A61B 1/00* (2006.01)
*A61B 1/07* (2006.01)
(Continued)

(52) U.S. Cl.
CPC ............ *A61L 29/041* (2013.01); *A61B 1/005* (2013.01); *A61B 1/0011* (2013.01);
(Continued)

(58) Field of Classification Search
CPC .............. A61B 1/0011; A61B 1/00165; A61B 1/00167; A61B 1/0017; A61B 1/07; A61B 5/0075
See application file for complete search history.

(56) References Cited

U.S. PATENT DOCUMENTS 5,210,814 A * 5/1993 McNally ............ A61B 1/00167
600/920
5,344,419 A * 9/1994 Spears ................ A61B 18/245
606/7

(Continued)

FOREIGN PATENT DOCUMENTS

| WO | 2011088580 A1 | 7/2011 |
| WO | 2014063257 A1 | 5/2014 |
| WO | 2014130736 A1 | 8/2014 |

OTHER PUBLICATIONS

Lima et al., Optical Fiber Catheter with Distal End Bending Mechanism Control for Raman Biospectroscopy, 2008, Instrumentation Science and Technology, vol. 36, pp. 43-55. (Year: 2008).*

(Continued)

*Primary Examiner* — Aaron B Fairchild
*Assistant Examiner* — Stephen Floyd London
(74) *Attorney, Agent, or Firm* — Todd A. Rattray; Oyen Wiggs Green & Mutala LLP

(57) ABSTRACT

A Raman endoscope for use in obtaining in vivo Raman spectra in the peripheral airways of the lungs and a method of constructing the Raman endoscope are disclosed. The endoscope has a tubular sheath containing a fiber bundle. The sheath has an outer diameter of less than 1.35 mm. The sheath is made of fluorinated ethylene propylene. The sheath is flexible along its length from a first end to a point along the sheath so that it can navigate sharp turns within the peripheral airways. A layer of coating covers the sheath along a terminal length and a probe tip of the fiber bundle.

(Continued)

The terminal length extends along a length of the sheath extending from a second end opposite to the first end to the point. Terminal length is rigid to facilitate advancement of the endoscope towards the lesion of interest. Terminal length is 5 mm or less.

15 Claims, 9 Drawing Sheets

(51) Int. Cl.
  *A61B 1/267* (2006.01)
  *A61B 5/00* (2006.01)
  *A61B 1/005* (2006.01)
  *A61L 29/04* (2006.01)

(52) U.S. Cl.
  CPC ...... *A61B 1/00117* (2013.01); *A61B 1/00126* (2013.01); *A61B 1/07* (2013.01); *A61B 1/2676* (2013.01); *A61B 5/0075* (2013.01); *A61B 1/00165* (2013.01)

(56) References Cited

U.S. PATENT DOCUMENTS

| | | | |
|---|---|---|---|
| 7,508,524 B2 | 3/2009 | Mahadevan-Jansen et al. | |
| 8,874,230 B2 | 10/2014 | Niver et al. | |
| 2003/0191398 A1 | 10/2003 | Motz et al. | |
| 2004/0151466 A1* | 8/2004 | Crossman-Bosworth | G02B 6/25 385/140 |
| 2004/0152992 A1 | 8/2004 | Zeng et al. | |
| 2005/0008869 A1* | 1/2005 | Clark | A61M 25/09 427/299 |
| 2008/0015558 A1* | 1/2008 | Harlan | A61B 1/0011 606/15 |
| 2008/0129993 A1* | 6/2008 | Brennan | G01J 3/44 600/478 |
| 2011/0165077 A1 | 7/2011 | Qian et al. | |
| 2011/0282166 A1* | 11/2011 | Chen | A61B 5/0084 600/478 |
| 2012/0022367 A1 | 1/2012 | Wong et al. | |
| 2013/0223802 A1* | 8/2013 | Dahmen | A61B 1/00167 156/196 |
| 2015/0018807 A1 | 1/2015 | Kircher et al. | |
| 2015/0105714 A1* | 4/2015 | Laudenslager | A61B 18/245 604/20 |
| 2015/0245768 A1* | 9/2015 | Hasegawa | A61B 5/0066 356/479 |
| 2015/0377787 A1* | 12/2015 | Zeng | A61B 5/0071 356/301 |
| 2019/0079255 A1* | 3/2019 | Miyamoto | G02B 6/02042 |
| 2019/0175005 A1* | 6/2019 | Tanaka | A61B 1/0011 |
| 2020/0000341 A1* | 1/2020 | Messerschmidt | G02B 23/2469 |

OTHER PUBLICATIONS

Cambridge University Engineering Department, Materials Data Book, 2003, pp. 1-37 (Year: 2003).*
Okagbare, P.I. et al., "Polymer-capped fiber-optic Raman probe for non-invasive Raman spectroscopy". Analyst Jan. 7, 2012; 137(1):77-81.
https://www.leoni-fiber-optics.com/en/products-and-services/optical-components/optical-probes/ (retrieved Dec. 19, 2018).
https://en.wikipedia.org/wiki/Fluorinated_ethylene_propylene (retreived Dec. 19, 2018).
Lam, S. et al., "Detection and Localization of Early Lung Cancer by Fluorescence Bronchoscopy", Cancer, 2000; 89: 2468-2473.
McGregor, H. C., et al. Real-time endoscopic Raman spectroscopy for in vivo early lung cancer detection, Journal of Biophotonics, 2017; 10: 98-110.
Savitzky, A. et al., "Smoothing and Differentiation of Data by Simplified Least Squares Procedures", Analytical Chemistry (1964) 36:1627-1639.
Zhao, J. et al., "Automated Autofluorescence Background Subtraction Algorithm for Biomedical Raman Spectroscopy", Appl Spectrosc, 2007; 61: 1225-1232.
Short, M.A. et al., "Development and in vivo testing of a high frequency endoscopic Raman spectroscopy system for potential applications in the detection of early colonic neoplasia", Journal of Biophotonics, 2016; 18:44-48.
Huang, N. et al., "Full range characterization of the Raman spectra of organs in a murine model", Optics Express, 2011; 19:22892-22909.
Short, M.A. et al., "Using high frequency Raman spectra for colonic neoplasia detection", Optics Express, vol. 21, No. 4, Feb. 21, 2013.

* cited by examiner

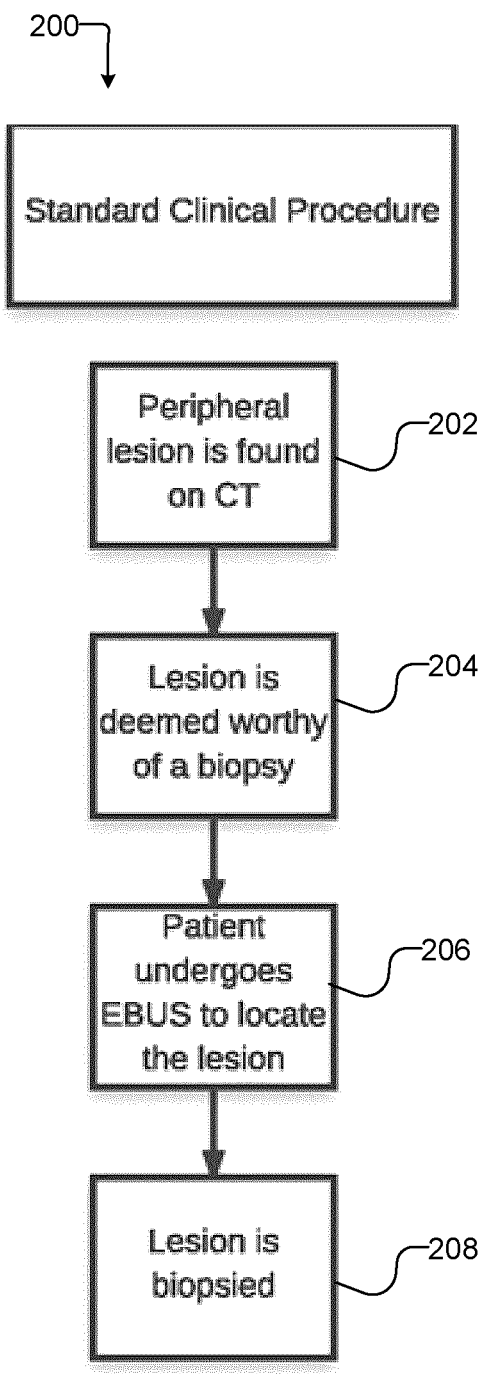
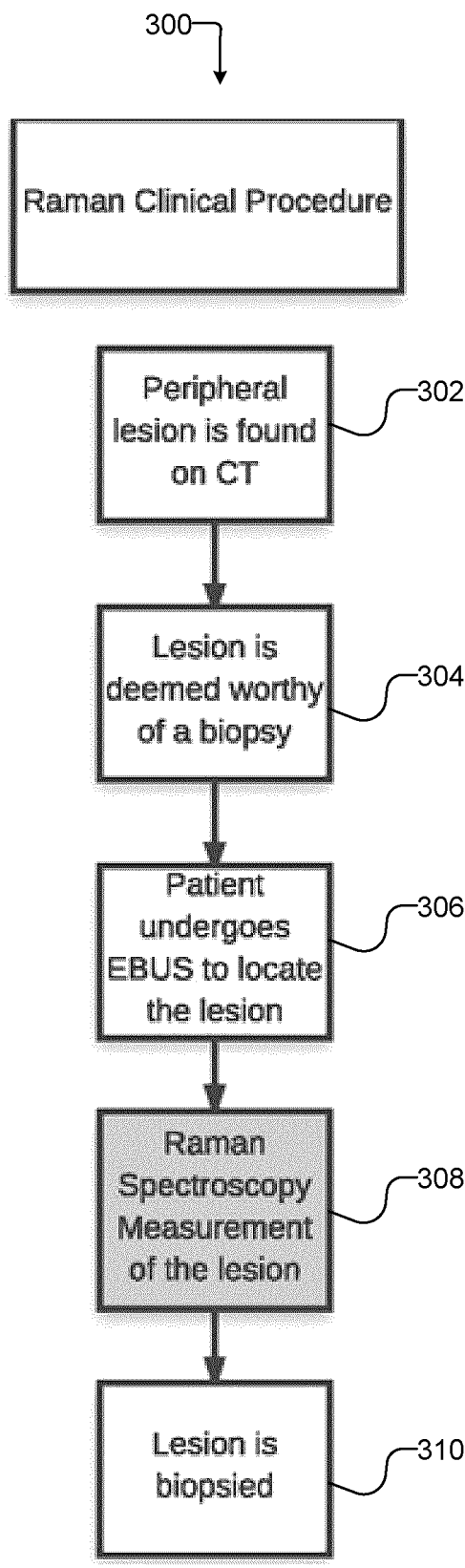
FIGURE 5A  FIGURE 5B

ENDOSCOPIC RAMAN SPECTROSCOPY DEVICE

CROSS-REFERENCE TO RELATED APPLICATIONS

This application claims priority from U.S. application Ser. No. 62/621,666 filed 25 Jan. 2018 entitled ENDOSCOPIC RAMAN SPECTROSCOPY DEVICE. For purposes of the United States, this application claims the benefit under 35 U.S.C. § 119 of U.S. application Ser. No. 62/621,666 filed 25 Jan. 2018, which is hereby incorporated herein by reference for all purposes.

FIELD

The invention relates generally to an apparatus and methods for the characterization of tissues. Specific embodiments provide apparatuses and methods useful for assessing peripheral lung tissues for cancer.

BACKGROUND

Lung cancer has one of the worst five-year survival rates of all cancers, at about 15%. The low survival rate is due to the detection of the disease at a late stage where there are fewer and less effective therapies.

Low-dose computed tomography imaging (CT) for lung cancer screening has recently been implemented to improve prognosis. Nodules that are identified in a CT scan are then biopsied to determine the next course of action. Biopsies may be performed by a transthoracic needle aspiration, or for nodules accessible from the lung airways, by using forceps during a bronchoscopy procedure.

Current clinical diagnostic methods for detecting lung cancer include white light bronchoscopy (WLB) and auto fluorescence bronchoscopy (AFB). For many years, WLB+AFB have been used to localize small lung lesions for biopsy in the central airways as described in Lam, S., MacAulay, C., leRiche, J. C. & Palcic, B. *Detection and localization of early lung cancer by fluorescence bronchoscopy*, Cancer, 2000; 89: 2468-2473. However, flexible bronchoscopes are generally unable to extend into the narrow peripheral airways of the lungs to provide visual information. Endobronchial radial ultrasound (R-EBUS) is commonly used to localize nodules requiring biopsy in the peripheral airways. However, obtaining a biopsy in the peripheral airways is complicated by a lack of direct visual guidance. As a result, multiple biopsies are often taken at the same location to ensure an accurate diagnosis. This process has potential adverse effects on the patient.

In general, the current method for obtaining a biopsy of a peripheral lung nodule during a bronchoscopy is unreliable with low diagnostic yield and high false positive rates. Yet, the majority of nodules found with CT are located in the peripheral airways. Thus there is a need to develop new clinical technologies which are capable of providing more reliable information to guide biopsy for peripheral regions of the lung.

Raman spectroscopy involves directing light at a tissue specimen. Some of the light scatters inelastically from the tissue specimen. Inelastic interactions with the tissue specimens can cause the scattered light to have wavelengths that are shifted relative to the wavelength of the incident light (Raman shift). The wavelength spectrum of the scattered light (the Raman spectrum) contains information about the nature of the tissue specimen. Analysis of the Raman spectrum can provide detailed biochemical information about the tissue.

Raman spectroscopy has been used during a bronchoscopy of the central lung airways as described in McGregor, H. C., Short, M. A., McWilliams, A. et al. *Real-time endoscopic Raman spectroscopy for in vivo early lung cancer detection*, Journal of Biophotonics, 2017; 10: 98-110.

There are very important differences between the central airways and the peripheral airways. In the peripheral airways, the tissue layers are thinner due to the absence of cartilage in the peripheral airways. Peripheral airways also have much smaller diameters than the central airways. It is not possible to navigate larger endoscopes along the small peripheral airways. In addition, lung cancers that arise in the peripheral airways are often of a different subtype than lung cancers in the central airway. Thus, technologies for application in the central airways may not be applicable to the peripheral airways.

A sensitive, specific non-invasive tool and method of obtaining information about lung lesions in the peripheral airways would provide a valuable adjunct to current clinical diagnostic methods.

SUMMARY

One aspect of the present invention provides an endoscope for obtaining in vivo Raman spectra from tissues in the peripheral airways of the lungs. Such endoscope has a small diameter in order to pass through the narrow peripheral airways of the lungs. Such endoscope is also flexible to navigate the twisty airways but maintain rigidity near a probe tip end to advance the endoscope forward towards the lesion of interest. Another aspect of the present invention provides methods for constructing the endoscope.

In some embodiments, the endoscope has a fiber bundle which extends along a lumen of a sheath between a first and an opposing second end of the sheath. A probe tip of the fiber bundle may project outwardly from the second end. The sheath has a small outer diameter. In example embodiments, the sheath has an outer diameter of about 1.35 mm or less. The sheath may be made of fluorinated ethylene propylene (FEP). The sheath is flexible along its length from the first end to a point along the sheath. Such portion of the sheath may have a minimum bend radius of approximately 20 mm or less.

In some embodiments, the probe tip is sealed with a layer of coating to provide rigidity to the terminus of the endoscope. In some embodiments, a terminal length of the sheath is also sealed. In example embodiments, terminal length is 5 mm or less. In some embodiments, the first end of the sheath is also sealed to a proximal end of the fiber bundle. Sealing at both ends of the sheath create a water-tight seal of the fiber bundle. In example embodiments, the layer of coating is epoxy. The epoxy may be pre-cured before application to the endoscope to control the rigidity of the endoscope.

In some embodiments, the FEP sheath is modified by a chemical etching process before sealing with the layer of coating. Chemical etching of the sheath facilitates bonding of epoxy onto the sheath. The FEP sheath may be chemically etched at the first end and the terminal length.

In some embodiments, the endoscope is constructed without a stiff metal ferrule near the probe tip. The absence of the stiff ferrule maintains the flexibility of the endoscope to allow the device to navigate through sharp turns in the peripheral airways.

Another aspect of the invention provides an endoscope suitable for use in passages of the periphery of the lungs. The endoscope includes at least one excitation optical fiber, a plurality of collection optical fibers and a sheath. The at least one excitation optical fiber has a coupling at a proximal end for connecting the excitation optical fiber to an output of a light source. The excitation optical fiber may have a diameter in the range of about 100 to 200 µm. The plurality of collection optical fibers may extend to a coupling at a proximal end for connecting the collection optical fibers to an input of a spectrograph. Each of the collection optical fibers may have a diameter in the range of approximately 50 to 200 µm.

The sheath has a bore. The bore of the sheath encloses distal ends of the excitation optical fiber and the plurality of collection optical fibers from a probe tip at the distal ends of the excitation optical fiber and the collection optical fibers for a distance of at least 30 cm along the optical fibers. The sheath may comprise a tube of a heat shrink FEP material. The sheath may have an outer diameter of not more than 1.35 mm. The sheath and the contained excitation and collection optical fibers are bendable with a bend radius of 20 mm or less while maintaining a light transmissivity along the excitation optical fiber and the plurality of collection optical fibers of not less than 90% of a light transmissivity when the sheath and contained optical fibers are straight.

The probe tip of the optical fibers may have a cured adhesive bonded to the end portions of the optical fibers and to a chemically etched end portion of the sheath. The cured adhesive is bonded to the optical fibers over a distance of not more than 5 mm from the ends of the optical fibers. The distal end of the probe tip may be polished. The probe tip may be exposing the ends of the optical fibers.

The distal end of the excitation optical fiber may be centered in the probe tip. The distal ends of the collection optical fibers may be arranged symmetrically around the distal end of the excitation optical fiber in a plurality of rings. The sheath and the optical fibers are free to move longitudinally relative to one another and to an inner wall of the sheath in response to bending of the endoscope.

Another aspect of the present invention provides an endoscope for use in conjunction with existing equipment used to localize nodules within the lungs. Such endoscope is capable of channeling through a guide sheath which typically has a small inner diameter of 1.4 mm or less. Such endoscope is also constructed from a material which has a low coefficient of friction with the plastic of a guide sheath to allow the endoscope to slide through the guide sheath. In example embodiments, the coefficient of friction of the endoscope is approximately 0.04 to 0.06.

Another aspect of the invention provides an endoscope for use with detecting lung cancers in the peripheral airways. A further aspect of the invention provides an endoscope for use with detecting benign nodules in the peripheral airways. Examples of benign nodules include nodules caused by fungal infections.

In addition to the exemplary aspects and embodiments described above, further aspects and example embodiments are illustrated in the accompanying drawings and/or described in the following description.

BRIEF DESCRIPTION OF THE DRAWINGS

The accompanying drawings illustrate non-limiting example embodiments of the invention.

FIG. 5A is a flow chart depicting a method of a current standard clinical procedure for the detection of peripheral lung lesions. FIG. 5B is a flow chart depicting a method of incorporating Raman spectroscopy into a clinical procedure for the detection of peripheral lung lesions.

DETAILED DESCRIPTION

Throughout the following description, specific details are set forth in order to provide a more thorough understanding of the invention. However, the invention may be practiced without these particulars. In other instances, well known elements have not been shown or described in detail to avoid unnecessarily obscuring the invention. Accordingly, the specification and drawings are to be regarded in an illustrative, rather than a restrictive sense.

Figure 1:
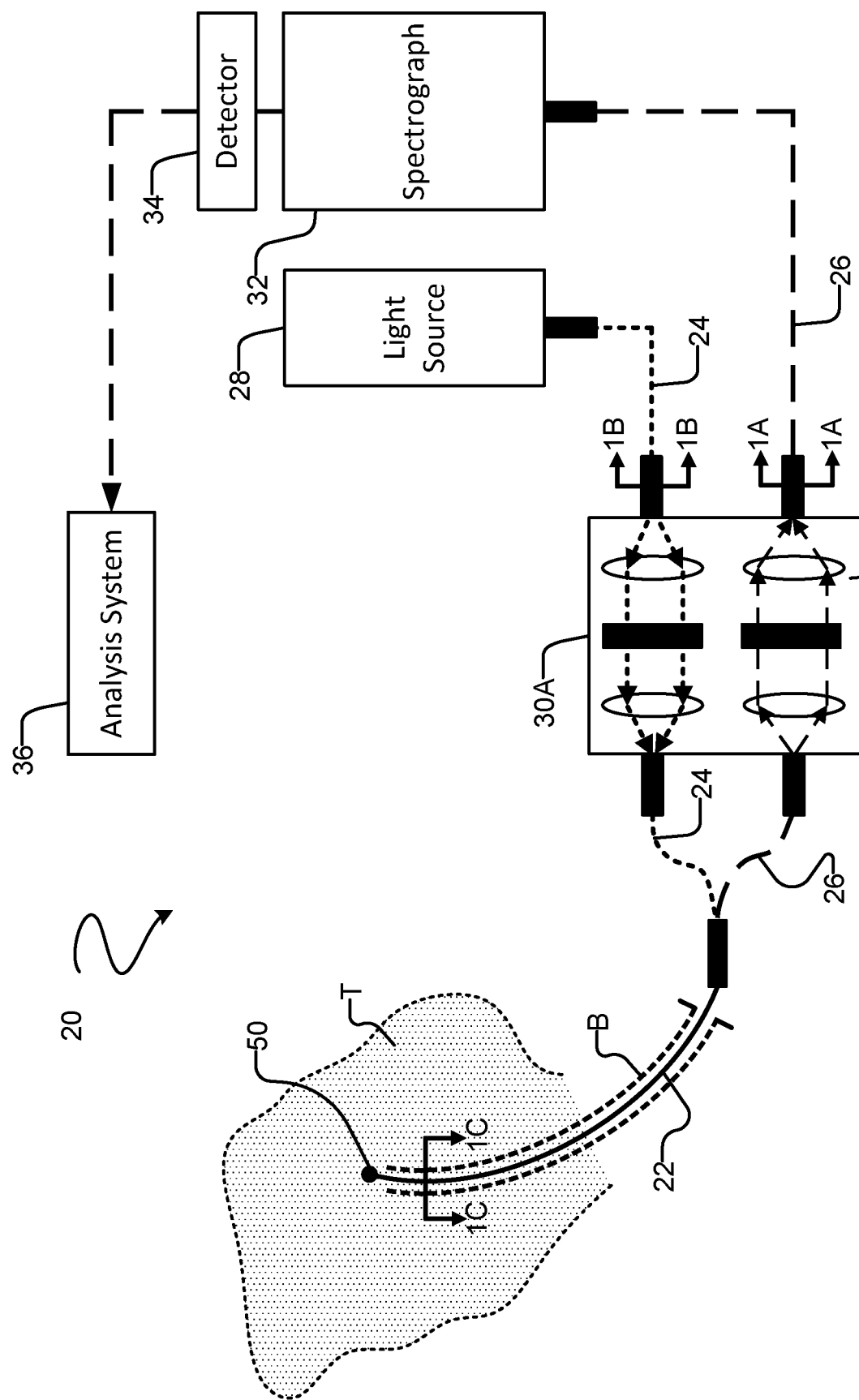
FIG. 1 is a schematic diagram of a Raman system according to an example embodiment of the invention.

FIG. 1 is a schematic diagram of a system 20 according to an example embodiment of the invention. System 20 comprises an endoscope 22, which is configured to extend down the instrument channel of a bronchoscope B for navigating a tissue T. Endoscope 22 comprises an excitation fiber 24 and one or more collection fibers 26. Excitation fiber 24 is connected to receive light from light source 28. Light from light source 28 is filtered by filter 30A and passes into endoscope 22. Light that emerges from the distal end 50 of endoscope 22 illuminates tissue T adjacent the end of endoscope 22 where some of the light undergoes Raman scattering. Some of the Raman scattered light enters endoscope 22 and is carried to spectrograph 32 by way of filter 30B via collection fibers 26. Spectrograph 32 and detector 34 work together to produce a Raman spectrum of the light incident at spectrograph 32. Information characterizing the Raman spectrum is then passed to a spectrum analysis system 36. In some embodiments, spectrum analysis system 36 operates in real time or near real time.

Light source 28 is a monochromatic light source and may, for example, comprise an infrared laser. In an example embodiment, the laser generates light having a wavelength of 785 nm. The excitation power may be controlled in real time, for example, from 0 to 300 mW.

Spectrograph 32 may comprise a grating. The grating may be of a holographic reflection type. Spectrograph 32 separates light having different wavelengths (i.e. different Raman shifts). A prototype embodiment used a spectrometer that could be manually tuned to an approximately 2000 cm$^{-1}$ wide spectral window anywhere within a Raman shift wavenumber range of 0 to 3400 cm$^{-1}$. In some embodiments, the grating has a custom range of, for example, 1350 to 3050 cm$^{-1}$.

Detector 34 may, for example, comprise a charged coupled device (CCD). Any suitable CCD may be used. In some embodiments, the CCD is cooled to about −70° C. in use. A thermoelectric cooler may be provided to cool detector 34.

Obtaining in vivo Raman spectra from tissues in the peripheral airways of the lungs can be challenging due to the architecture of the lung. The peripheral airways have much smaller diameters than the central airways. In addition, the divisions of the airways separating the left and right lungs, and the further divisions of the left and right lungs into the respective lobes result in sharp turns inside the peripheral airways. Prior art Raman endoscopes are not designed to navigate the lung architecture of peripheral regions of the lungs. Prior art Raman endoscopes tend to be too large and not flexible enough to safely navigate the peripheral airways.

It is desirable to provide a Raman endoscope that is capable of being used in conjunction with existing equipment used to localize nodules deep within the lungs. For example, the endoscope may be deployed through a guide sheath. The guide sheath serves as a lesion locator to direct tools such as biopsy forceps to the identified lesion.

Guide sheaths for use in peripheral regions of the lungs have small inner diameters. For example, some guide sheaths have inner diameters of approximately 1.4 mm or less. The small inner diameter of the guide sheath imposes size restrictions on the endoscope. Guide sheaths may be constructed of plastic. The plastic construction of the guide sheath imposes restrictions on the material that can be used to construct Raman endoscopes. Prior art endoscopes are generally made of plastic. If the plastic of the endoscope does not have a low enough coefficient of friction with the plastic of a guide sheath then it may be difficult or impossible to advance the endoscope along the guide sheath. This problem is made much worse when the endoscope is very small in diameter.

A further challenge is the inherently weak Raman signals. The endoscope must be capable of capturing and delivering to spectrograph 32 measuring the relatively weak Raman signal with good signal to noise ratio even when the endoscope is curved to follow twisting peripheral airways.

The aforementioned issues must be addressed in designing a Raman endoscope for applications in the peripheral lungs. Given the unique challenges addressed above, a Raman endoscope useful for application in other tissues or even in a different region of the lungs would not be useful for application in the peripheral lungs.

An aspect of this invention relates to an endoscope for use in the peripheral airways of the lungs. The endoscope has a diameter of 1.35 mm or less such that the endoscope can navigate the small diameter of the peripheral airways on its own or by insertion through a guide sheath. The endoscope is also very flexible along its length so that it can navigate sharp turns within the airways while still efficiently carry light in both directions along the endoscope. For example, the endoscope may be bendable with a radius of curvature of about 20 mm or less while maintaining light loss of no more than about 10% in both directions. The endoscope must be longitudinally stiff enough so that it can be pushed through a guide sheath to advance the distal end of the endoscope towards a lesion of interest to transmit and collect light to and from a tissue surface. A surface of the endoscope preferably has a low coefficient of friction with plastics of the types used for guide sheaths.

In some embodiments, the endoscope comprises a distal end and an opposing proximal end. The endoscope comprises a sheath having an outer diameter of less than 1.35 mm. The sheath may extend along a length of the distal end. The length of the distal end may, for example, be approximately 130 cm. A fiber bundle is contained within the sheath. The fiber bundle includes at least one excitation fiber and a plurality of collection fibers. In some embodiments, the fiber bundle includes 31 collection fibers. Tips of the excitation fiber and collection fibers may be exposed at the distal end of the endoscope. Each of the excitation fibers and collection fibers may have a numerical aperture of about 0.22. The minimum bend radius of the individual excitation fibers and the collection fibers may be about 20 mm or less.

The endoscope is sealed at the distal end. The sealing should allow the portions of the endoscope that are near the distal end to remain flexible. For example, in some embodiments the sealing is provided by an adhesive bonded to the sheath and the contained optical fibers. The adhesive may be present only in the endmost 5 mm or less of the endoscope. In some embodiments, an end of the sheath opposite to the distal end may also be sealed to proximal ends of the optical fibers. The sealing of both ends of the endoscope prevents entry of water or other fluids during use and cleaning of the endoscope. The adhesive may comprise an epoxy. In some embodiments, the epoxy is partially pre-cured prior to application to the endoscope.

Figure 2:
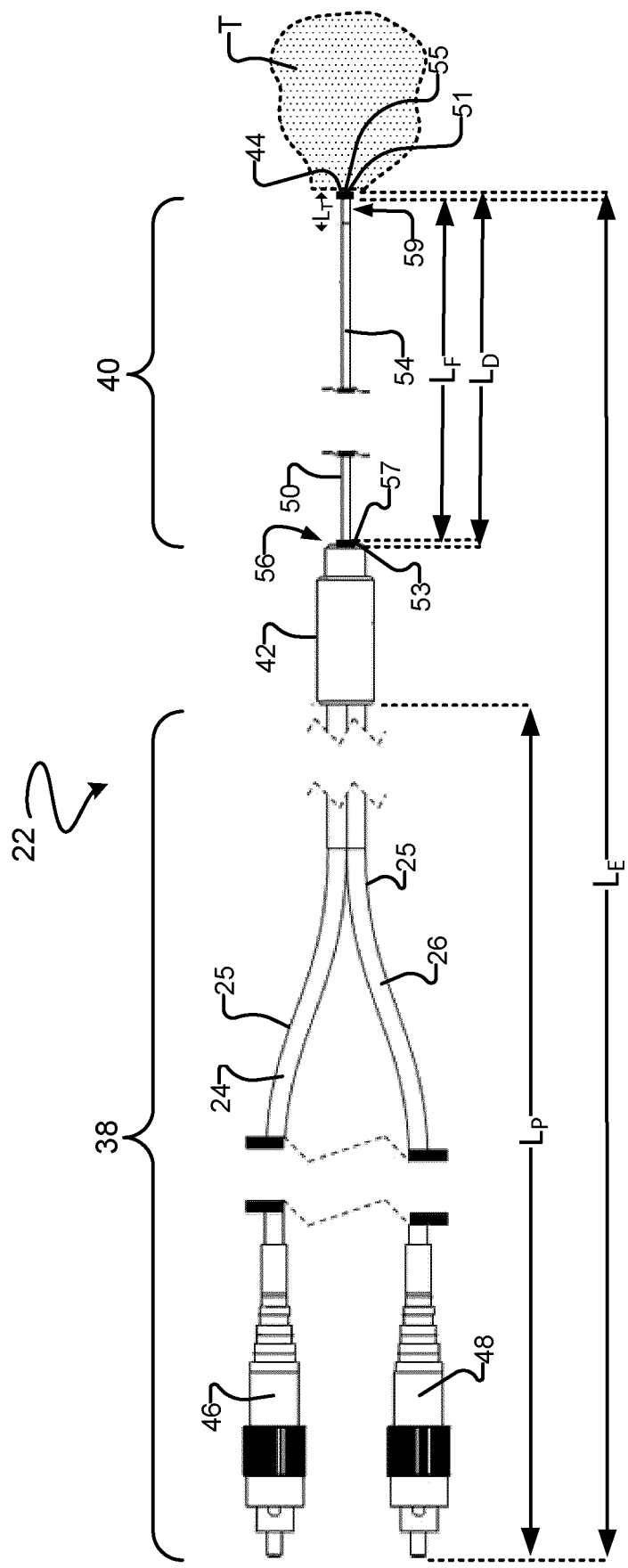
FIG. 2 is a plan view of a Raman endoscope of the FIG. 1 Raman system.

FIG. 2 is a plan view of an endoscope according to an example embodiment of the invention. Endoscope 22 comprises a proximal end 38 and an opposing distal end 40. Proximal end 38 and distal end 40 may be separated by a junction block 42. Distal end 40 comprises a probe tip 44 at its terminal end opposite to junction block 42. Probe tip 44 may be positioned adjacent to tissue T.

Figure 1A:
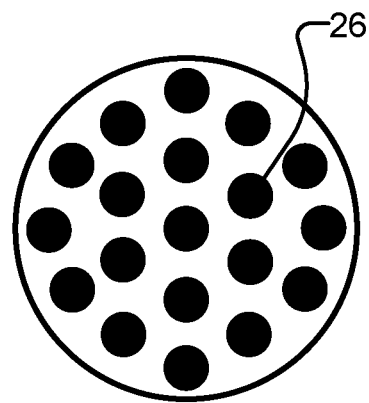
FIG. 1A is a cross-sectional view taken along the line 1A-1A of FIG. 1.
Figure 1B:
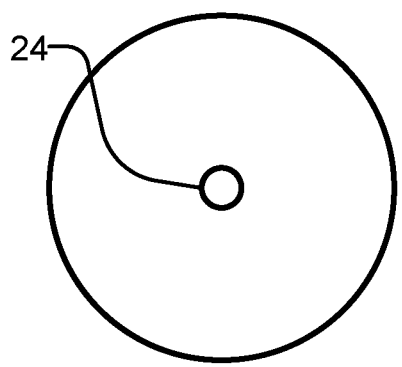
FIG. 1B is a cross-sectional view taken along the line 1B-1B of FIG. 1.
Figure 1C:
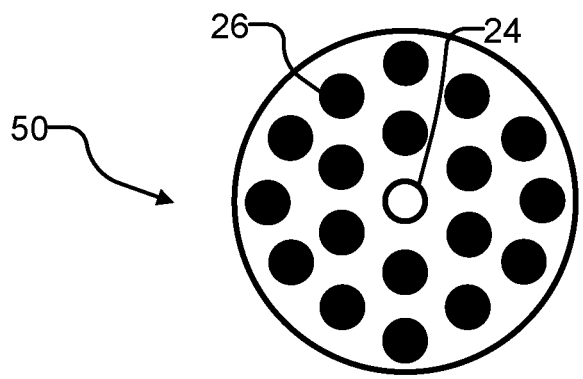
FIG. 1C is a cross-sectional view taken along the line 1C-1C of FIG. 1.

Endoscope 22 includes an excitation fiber 24 and a plurality of collection fibers 26 (as best shown in FIGS. 1A, 1B and 1C). Excitation fiber 24 is configured to deliver light to illuminate tissue T. Collection fibers 26 are configured to receive Raman scattered light from tissue T.

At proximal end 38 of endoscope 22, excitation fiber 24 is separated from collection fibers 26. Excitation fiber 24 can be coupled to a light source and collection fibers 26 may be coupled to a spectrograph. Excitation fiber 24 and collection fibers 26 may separately be encased in opaque jackets (e.g. tubular stainless steel jackets 25). Fiber-optic (FC) connectors 46, 48 may be used to couple fibers 24, 26 respectively to the light source and spectrograph.

Figure 3A:
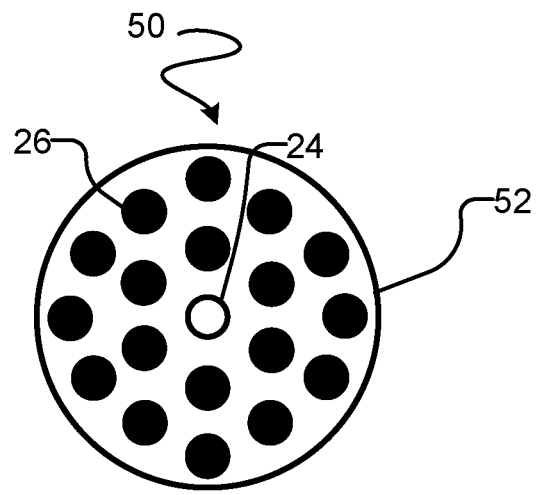
FIG. 3A is an end plan view of a fiber bundle of the FIG. 2 Raman endoscope.

Collection fibers 26 may be distributed around a periphery of excitation fiber 24 to form a fiber bundle 50 at least along a length $L_D$ of distal end 40. FIG. 1C and FIG. 3A are end plan views of fiber bundle 50 according to an example embodiment. In some embodiments, excitation fiber 24 is positioned at a radial center C. In some embodiments, excitation fiber 24 is at a radially off-center position within fiber bundle 50. Excitation fiber 24 may be surrounded by one or more radial layers of collection fibers 26.

Fiber bundle 50 may be arranged in a circle at a probe tip end 51 of distal end 40. Collection fibers 26 may be arranged in a linear arrangement at an entrance aperture of a spectrometer. For example, collection fibers 26 of the linear array may be arranged along a parabolic curve. It has been demonstrated that such a configuration corrects the spectrograph image and increases the signal to noise ratio and spectral resolution.

In some embodiments, 24 to 31 collection fibers 26 are arranged around a periphery of excitation fiber 24. In an example embodiment, 31 collection fibers 26 are arranged around a periphery of excitation fiber 24. Collection fibers 26 may be arranged in one or more radial layers around excitation fiber 24. In an example embodiment, collection fibers 26 may be arranged in three radial layers around excitation fiber 24. In such example embodiment, fiber bundle 50 comprises an outermost layer having 17 collection fibers 26, a middle layer having 11 collection fibers 26 and an innermost layer closest to excitation fiber 24 having 3 collection fibers 26.

In some embodiments, the diameter of excitation fiber 24 is in a range of approximately 100 to 200 µm. In some embodiments, the diameter of excitation fiber 24 is approximately 100 µm. In some embodiments, the diameter of each of the one or more collection fibers 26 is in the range of approximately 50 to 200 µm. In some embodiments, the diameter of each of the one or more collection fibers 26 is approximately 105 µm. In some embodiments, the diameter of fiber bundle 50 is about 1.35 mm or less.

Figure 3B:
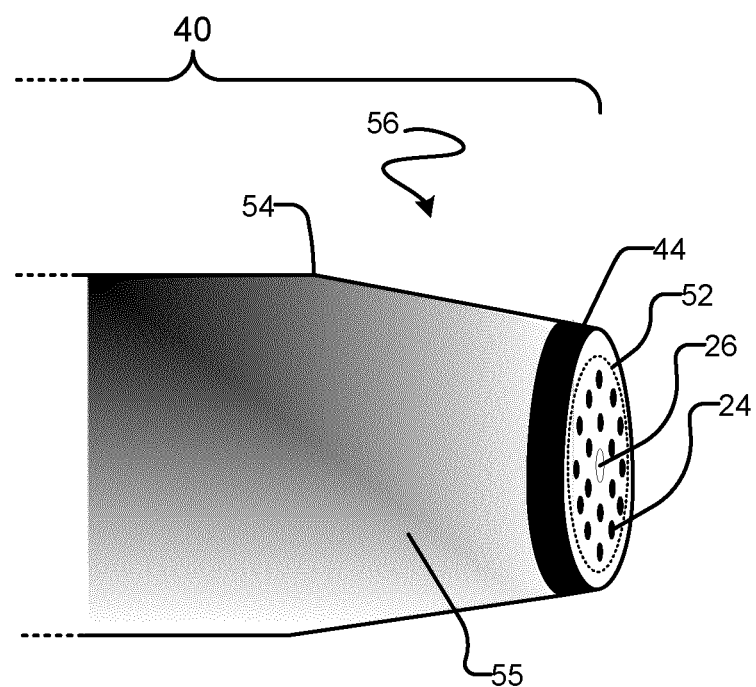
FIG. 3B is a side view of the fiber bundle of FIG. 3A encased in a tubular sheath.

Referring to FIG. 3B, fiber bundle 50 is encased in a tubular sheath 54. Tubular sheath 54 may encase an outer layer 52 of fiber bundle 50 loosely enough to allow optical fibers 24 and/or 26 to slide longitudinally relative to one another as sheath 54 is flexed to follow curves. In some embodiments, an outer diameter of tubular sheath 54 is in the range of about 0.5 mm to 1.5 mm. In some embodiments, the outer diameter of tubular sheath 54 is about 1.35 mm or less. In an example embodiment, tubular sheath 54 extends along a length $L_D$ of distal end 40. In some embodiments, tubular sheath 54 extends along a portion of length $L_D$.

Sheath 54 may be made of a heat shrinkable material. The material may, for example, have a heat shrink ratio of about 1.6:1. In an example embodiment, optical fibers 24, 26 are passed through the heat shrinkable sheath 54 and then the sheath is heated sufficiently to shrink the sheath around the optical fibers, thereby providing an endoscopy body having a suitably small diameter. Heating conditions (such as temperature and time) that are compatible with the properties of optical fibers 24, 26 are used in the heat shrinking process.

Tubular sheath 54 may advantageously be constructed from a fluorinated ethylene propylene (FEP) copolymer. The inventors have determined that FEP facilitates making an endoscope having a small diameter that is very flexible and also has a low coefficient of friction with most plastics. These properties facilitate smooth navigation of passages of the peripheral airways of the lungs. In an example case the FEP sheath is heat shrinkable, has an inside diameter before heating of 1.4 mm, an inside diameter after heating of 0.84 mm and a wall thickness of 0.203 mm. Advantageously, FEP is a biocompatible material which is suitable for insertion into human subjects.

Tubular sheath 54 may have a wall thickness in a range of approximately 0.2 to 1 mm. Tubular sheath 54 may have a flexural modulus of approximately 530 to 640 GPa. Tubular sheath 54 may have a coefficient of friction with approximately 0.04 to 0.06.

As discussed above, a first end 57 of sheath 54 and an opposing probe tip end 51 of endoscope 22 are sealed. Probe tip end 51 includes probe tip 44. Probe tip end 51 may include a length of sheath 54. Sealing may be achieved by filling spaces between fibers 24, 26 in first and second end segments 56, 59 of endoscope 22 with a curable sealant. Second end segment 59 extends along a distal terminal length $L_T$. Distal terminal length $L_T$ extends along a portion of length $L_D$ of distal end 40. Terminal length $L_T$ may, for example, have a length of approximately 5 mm or less. The sealant does not bond optical fibers 24, 26 to sheath 54 along a flexible length $L_F$. Flexible length $L_F$ extends along a length $L_D$ of distal end 40 between first end 57 and probe tip end 51.

By only providing sealant at first end 57 of sheath 54 and probe tip end 51 as opposed to sealing fiber bundle 50 to sheath 54 along the entire length $L_D$ of distal end 40, a small minimum bend radius of sheath 54 can be achieved. This is because, between the ends of the endoscope, the optical fibers can move relative to one another and sheath 54 (e.g. by sliding longitudinally relative to one another and the wall of sheath 54). Sealing a proximal end 53 of fiber bundle 50 and probe tip 44 creates a water-tight seal of fiber bundle 50. The water-tight seal allows the endoscope to be re-usable between patients upon disinfection after use.

Referring to FIG. 2, a diameter of probe tip 44 may be made slightly greater than a diameter of sheath 54 due to the presence of the sealant. In an example embodiment, the sealant is an epoxy adhesive. The epoxy adhesive may be pre-cured prior to sealing. In an example embodiment, the epoxy adhesive is pre-cured for approximately 20 minutes. Pre-curing of the epoxy adhesive reduces wicking of the epoxy along endoscope 22 between fibers 24 and 26. Pre-curing of the epoxy adhesive increases its viscosity. The inventors have determined that reducing untended wicking of the epoxy facilitates controlling the rigidity of the endoscope in the vicinity of the probe tip as required for advancing through sharp turns in the peripheral airways. Specifically, the sealing only increases stiffness of a very short section of the endoscope.

As noted above, sheath 54 may be made of a material such as FEP, which has low bondability with epoxies or other sealants. In such embodiments, the surface of sheath 54 may be modified through a chemical process to allow sheath 54 to physically bond with the layer of coating. In an example embodiment, sheath 54 is chemically modified along distal terminal length $L_T$ and first end 57. The chemical process may be chemical etching. In the embodiment where sheath 54 is made of FEP, the chemical etching process may involve removing fluorine atoms at the surface layer of the fluoropolymer and forming a carbonaceous layer on the material for bonding to the coating. In an example embodiment, a sodium-based etching solution commercially available under the product name, FluoroEtch® Safety Solvent, is used to etch a FEP sheath. In an example embodiment, distal terminal length $L_T$ comprises a length of approximately 5 mm.

In some embodiments, a small portion of sheath 54 from distal end 40 is removed to expose fibers 24, 26 at probe tip 44 prior to sealing sheath 54 and probe tip 44. The removal of a portion of sheath 54 facilitates polishing of probe tip 44. Approximately 1-2 mm of sheath 54 may be removed. Final polishing of probe tip 44 may be performed to reduce optical losses at the fiber/air interfaces and thus to increase collection efficiency.

The length of proximal end 38 $L_P$ may, for example, be in a range of approximately 33 to 37 cm. The length of distal end 40 $L_D$ may be in a range of approximately 125 to 135 cm. In an example embodiment, length $L_P$ is 35 cm and $L_D$ is 130 cm. In some embodiments, the overall length of endoscope 22 $L_E$ is approximately 1 to 2.5 m.

Excitation fiber 24 and collection fibers 26 may comprise low —OH (hydroxyl) silica optical fibers. In an example embodiment, the minimum bend radius of each of collection fibers 26 is about 13 mm. The length of excitation fiber 24 and collection fibers 26 may be in a range of about 31 to 35 cm.

In some embodiments, excitation fiber 24 is coated with an opaque material to prevent cross-talk with collection fibers 26. For example, excitation fiber 24 may have an aluminum coating. In some embodiments, collection fibers 26 are coated with polyimide.

Certain prior art Raman endoscopes include a metal ferrule which extends along a length of the distal end near the probe tip. The metal ferrule was considered to be important for alignment of the excitation fiber to the center of the bundle, which has been shown to result in improved collection efficiency. The inventors have determined that a metal ferrule, which stiffens the endoscope for at least a length of the ferrule can impede navigation through the sharp turns in the peripheral airways. In an example embodiment, the distal tip portion of endoscope 22 does not comprise a stiff ferrule and is constructed to remain flexible close to distal end 40 such that a bend having a tight radius (e.g. a radius of curvature less than or equal to about 20 mm) may be formed at a distance of not more than about 5 mm from distal end 40.

Figure 4:
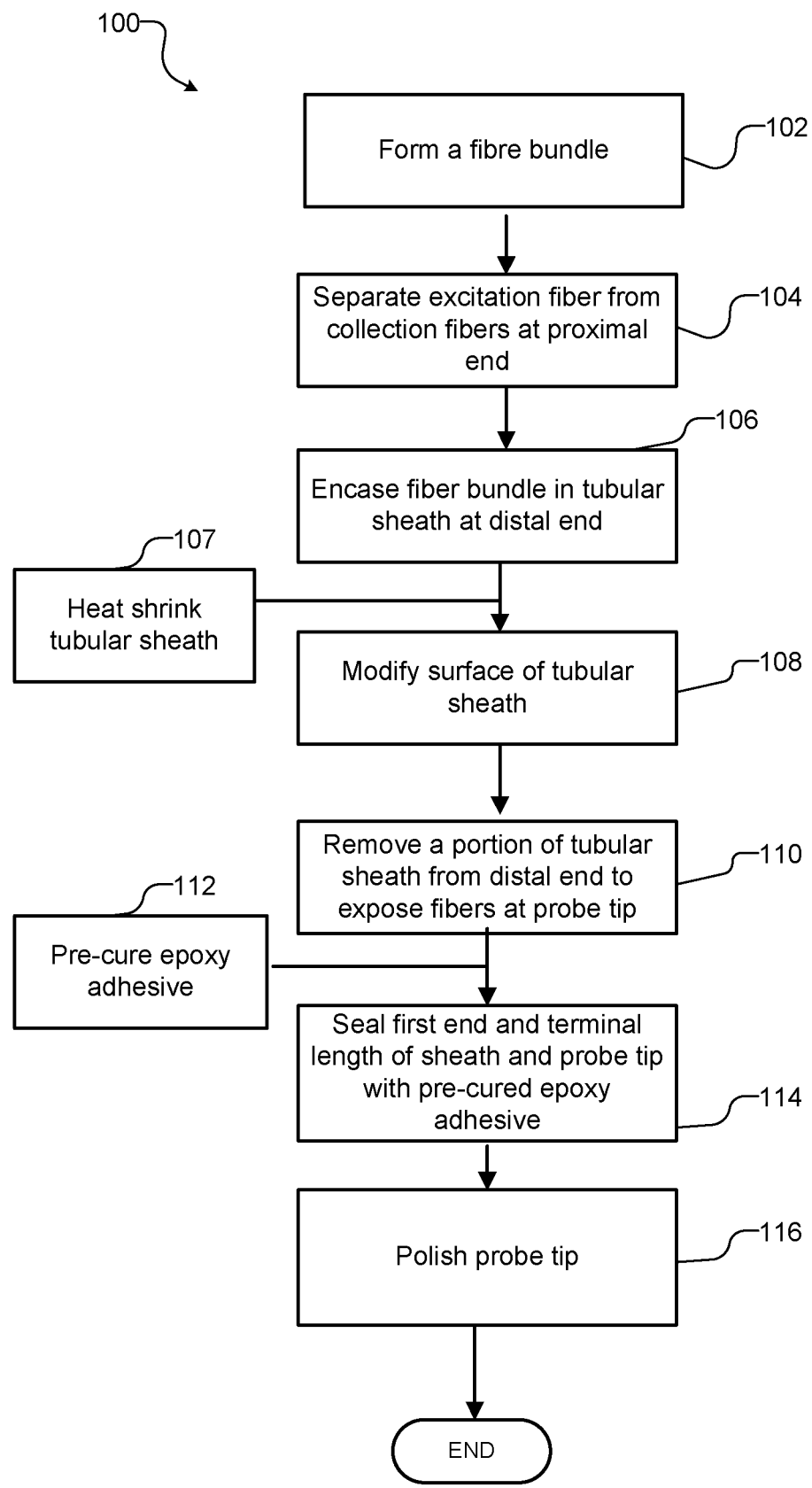
FIG. 4 is a flow chart illustrating a method of constructing the Raman endoscope of FIG. 2.

FIG. 4 is a flow chart depicting a method 100 for constructing a Raman endoscope for obtaining in vivo Raman spectra from the peripheral airways of the lungs according to an example embodiment of the invention. In block 102, a plurality of collection fibers are arranged around a periphery of a central excitation fiber to form a fiber bundle. In block 104, the excitation fiber is separated from the collection fibers at the proximal end so that the excitation fiber and the collection fibers can be connected to the light source and the spectrograph respectively. In block 106, the fiber bundle is encased in a tubular sheath at the distal end. In block 107, tubular sheath containing the fiber bundle may undergo a heat shrinking process. In block 108, a length of the outer surface of the tubular sheath near the probe tip and an end in the vicinity of a junction connecting the distal end to the proximal end of the endoscope is modified, for example through a chemical etching process, to improve bondability.

The chemical etching process may comprise removing fluorine atoms at the surface of the sheath to form a carbonaceous layer on the material that is compatible with an adhesive coating. Any suitable chemical etching method may be used. For example, chemical etching may comprise immersing the sheath in an etching solution for approximately 30 to 60 seconds. The etching solution may be commercially available under the product name Fluoro-Etch® Safety Solvent. The sheath may be rinsed in alcohol for about 5-20 seconds. The sheath may then be rinsed in hot non-chlorinated water for 15 to 30 seconds, followed by a rinse in hot mildly acidic water such as 2 to 5% acetic acid that is warmed to 70° C. for one minute. The sheath is then dried prior to sealing with a sealant such as epoxy adhesive.

In block 110, a small portion of the tubular sheath at the distal end is removed to expose the fibers at the probe tip. In block 112, the epoxy adhesive is pre-cured to reduce wicking. In an example embodiment, the epoxy adhesive is pre-cured by heating it in an oven at about 60° C. for approximately 20 minutes. In block 114, both ends of the tubular sheath and/or the probe tip are sealed with a layer of the epoxy adhesive. In block 116, the probe tip is polished.

FIG. 5A is a flow chart depicting a method 200 of a current standard clinical procedure for the detection of peripheral lung lesions. FIG. 5B is a flow chart depicting a method 300 which incorporates Raman spectroscopy into a clinical procedure for the detection of peripheral lung lesions. As shown in FIGS. 5A and 5B, the incorporation of Raman spectroscopy can be done with only small alterations to the standard clinical procedure.

In blocks 202 and 302, both procedures begin with a CT scan of the periphery of the lungs to locate a general location of a peripheral lesion that is considered worthy of a biopsy (blocks 204, 304). In blocks 206, 306, a patient undergoes an EBUS procedure to locate the lesion. Ultrasound images showing an approximate location of the lesion can be obtained upon performing an EBUS procedure. In the standard clinical procedure 200, a biopsy of a lesion is taken solely based on the approximate location of the lesion obtained through performing an EBUS procedure (block 208). The taking of multiple biopsies in the same location in the patient is undesirable but is frequently required in the standard clinical procedure.

In the Raman clinical procedure 300, a Raman spectroscopy measurement of the lesion is obtained to confirm the results of the EBUS procedure (block 308) prior to the biopsy (block 310). Confirmation by Raman spectroscopy eliminates the need to take multiple biopsies at the same location in a patient to ensure an accurate diagnosis.

FIG. 6 is a schematic diagram depicting a method 400 of locating a peripheral lesion according to an example embodiment of the invention. Method 400 is performed after information of the general location of the peripheral lesion is obtained from a CT scan. Referring to FIG. 6A, a guide sheath 402 is inserted into a peripheral airway 404 proximal to the general location of the peripheral lesion 406. Guide sheath 402 may be fitted within a length of the instrument channel in a bronchoscope (not shown). Guide sheath 402 is secured in place in the airway proximal to lesion 406 so as to direct further instruments to the proper location. A Radial-EBUS (R-EBUS) probe 408 is then inserted through guide sheath 402. R-EBUS probe 408 is configured to obtain ultrasound images of lesion 406.

Figure 6A:
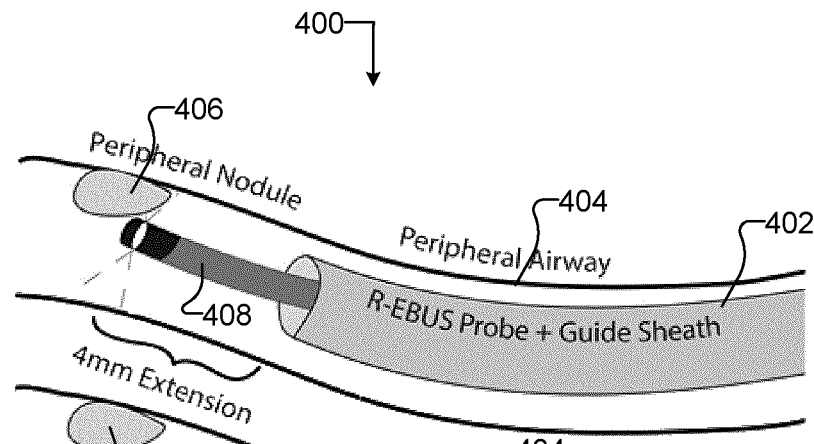
FIGS. 6A, 6B, 6C and 6D (collectively, FIG. 6) is a schematic diagram depicting a method of locating a peripheral lesion according to an example embodiment of the invention.
Figure 6B:
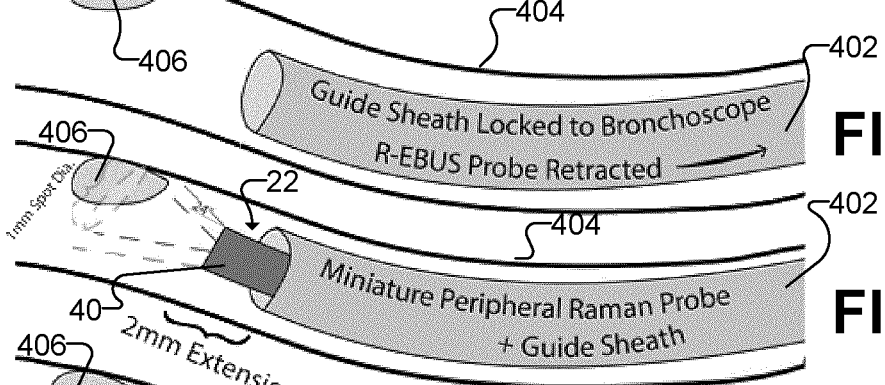
Figure 6C:
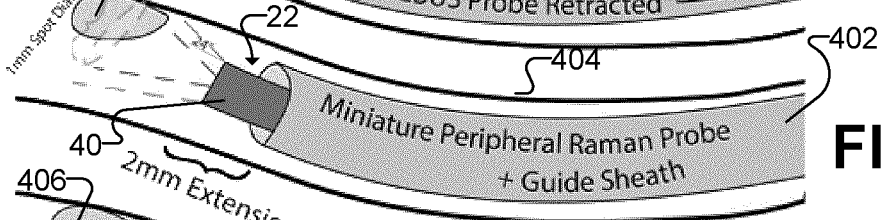

Referring to FIG. 6B, after ultrasound images of lesion 406 are taken, R-EBUS probe 408 is then retracted from guide sheath 402. Referring to FIG. 6C, Raman endoscope 22 is then inserted through guide sheath 402. Distal end 40 may project outwardly through terminal end 410 of guide sheath 402. In an example embodiment, approximately 2 mm of distal end 40 is extended through guide sheath 402 for advancement towards lesion 406. In an example embodiment, the angle at which light emerges from the excitation fiber is approximately 25°. In such embodiment, the numerical aperture (NA) of the optical fibers may be approximately 0.22.

Multiple measurements may be taken to obtain in vivo Raman spectra relating to the lesion of interest 406. In some embodiments, 15 to 20 measurements may be taken. The measurements may be taken with suitable integration times. In some embodiments, integration times on the order of 1 second are used. Real time spectra pre-processing may include the subtraction of the CCD dark count, followed by Raman shift and intensity calibration. Further processing may include a smoothing algorithm. In an example embodiment, a 13 point smoothing algorithm is used, as described in A. Savitzsky, M. J. Golay and M. J., *Smoothing and differentiation of data by simplified least squares procedures*, Analytical Chemistry (1964) 36: 1627-1639. Further processing may also include autofluorescence removal. In an example embodiment, autofluorescence removal may be performed by using a fitted iterative sixth order polynomial procedure as described in J. Zhao, H. Lui, D. I. McLean and H. Zeng *Automated autofluorescence background subtrac-* tion algorithm for biomedical Raman spectroscopy, Appl Spectrosc, 2007; 61: 1225-1232. The pure Raman spectra may then be normalized to the area under the curve. Processing techniques used to analyze the Raman spectra are further described in WO 2011/088580 to Zeng et al., entitled "Apparatus and Methods for Characterization of Lung Tissue by Raman Spectroscopy", which is hereby incorporated herein by reference.

Figure 6D:
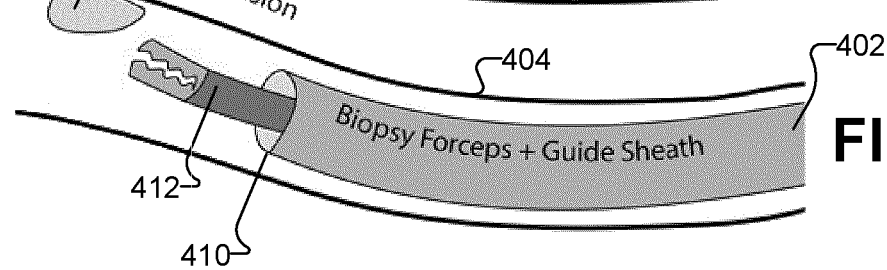

Referring to FIG. 6D, once measurements to obtain Raman spectra have been taken, endoscope 22 is retracted from guide sheath 402 and a biopsy forceps 412 may be inserted within guide sheath 402 to retrieve a sample of tissue from lesion 406.

While in vivo Raman spectra may be obtained using endoscope 22 for the detection of peripheral lung cancers, endoscope 22 may also be used in applications such as detecting benign nodules in the peripheral airways. Such benign nodules include, but not limited to, nodules caused by fungal infections.

The invention is further described with reference to the following specific example, which is not meant to limit the invention, but rather to further illustrate it.

Example 1

A Raman endoscope of the type illustrated in FIG. 2 and the Raman system of the type illustrated in FIG. 1 were used to collect real-time, in vivo spectra of lesions in the peripheral lungs of two patients. Raman spectra were obtained using the method illustrated in FIGS. 5B and 6.

Figure 7:
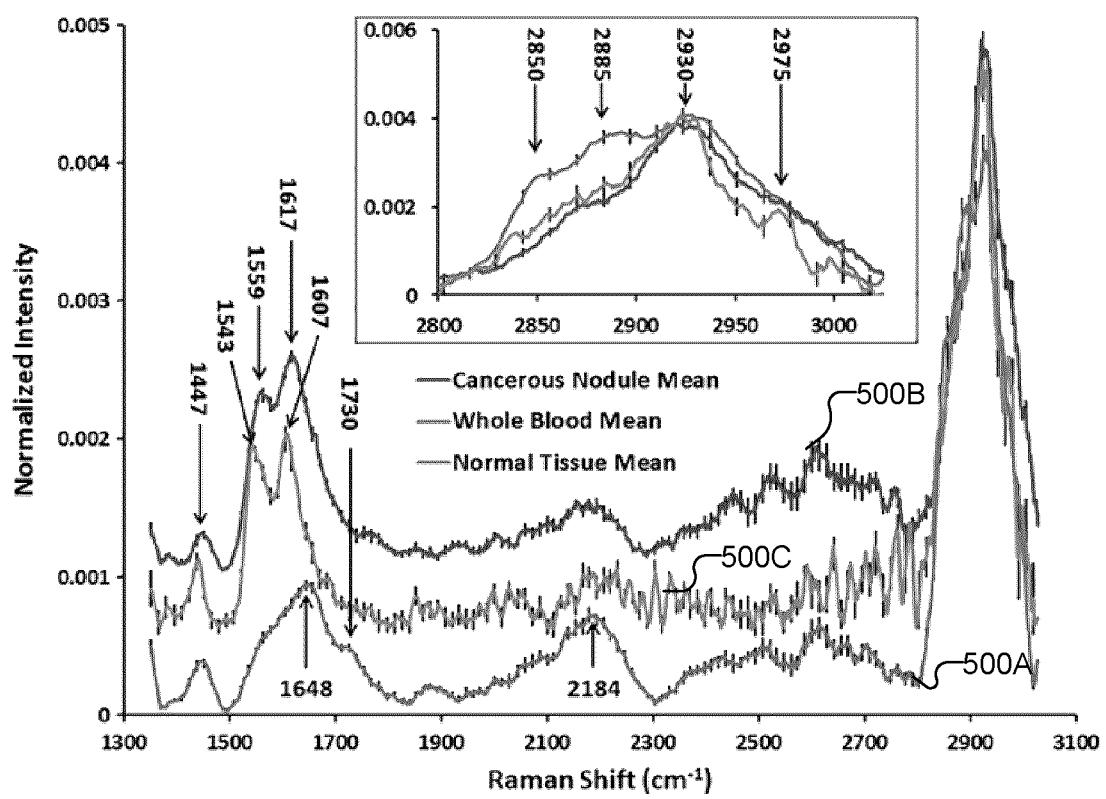
FIG. 7 is a graph of mean normalized Raman spectra from three pathology groups.

FIG. 7 shows the mean normalized Raman spectra obtained for each pathology type, specifically, normal airway tissue (curve 500A), cancerous nodules (curve 500B), and a whole blood reference sample (curve 500C). Differences between the cancerous and normal tissue can be seen in both the low frequency fingerprint region (1350-1800 $cm^{-1}$) and the high frequency region (2800-3060 $cm^{-1}$).

The most striking differences between the spectra of the normal and cancer group can be seen at the Raman peak located at 2887 $cm^{-1}$. The peak corresponds to the antisymmetric $CH_2$ vibrations of lipids. The inventors have determined that as pathology progresses to invasive lung cancer of peripheral lung tissues, the intensity of high frequency lipid peaks weaken as described in McGregor, H. C., Short, M. A., McWilliams, A. et al. *Real-time endoscopic Raman spectroscopy for in vivo early lung cancer detection*, Journal of Biophotonics 2017; 10: 98-110. The inventors have also discovered from in vivo colon measurements that this peak is reduced as pathology becomes more advanced, as described in Short, M. A., Wang, W., Tai, I. T. & Zeng, H. *Development and in vivo testing of a high frequency endoscopic Raman spectroscopy system for potential applications in the detection of early colonic neoplasia*, Journal of Biophotonics, 2016; 18: 44-48. Without being bound to any particular theory, it is hypothesized that the difference seen at the Raman peak located at 2887 $cm^{-1}$ is due to biochemical differences between lesions. The peaks at 2930 $cm^{-1}$ and 2954 $cm^{-1}$ have been assigned to the $CH_3$ vibration found in proteins.

The peaks in the low frequency region (1350-1800 $cm^{-1}$) also show differences between the pathology groups. Large peaks are seen at 1550 $cm^{-1}$ and 1615 $cm^{-1}$ in the cancerous tissue but these peaks are lessened in the normal tissue. The 1550 $cm^{-1}$ peak has been assigned as the amid II band, and the 1615 $cm^{-1}$ peak has been assigned as the C=C stretching mode found in proteins. These peaks are seen with a large contribution in blood spectra, as described in Huang, N. Short, M., Zhao, J. et al. *Full range characterization of the Raman spectra of organs in a murine model*, Optics express, 2011; 19: 22892-22909. Increased angiogenesis during tumor formation is also known as a cancer hallmark.

Differences in Raman spectra between the normal tissue (curve 500A) and the cancerous tissue (curve 500B) can be seen at the 1659 $cm^{-1}$ peak. The 1659 $cm^{-1}$ peak correspond to the amide 1 band. Little signal in this region is detected in the whole blood sample (curve 500C). As tissue pathology goes from a normal to a cancerous lesion, the 1659 $cm^{-1}$ peak becomes less intense. This may suggest that biochemical changes are occurring.

The 1442 $cm^{-1}$ peak was assigned to the $CH_2$ stretch. No Raman peaks were found between 1800 and 2800 $cm^{-1}$.

Figure 8:
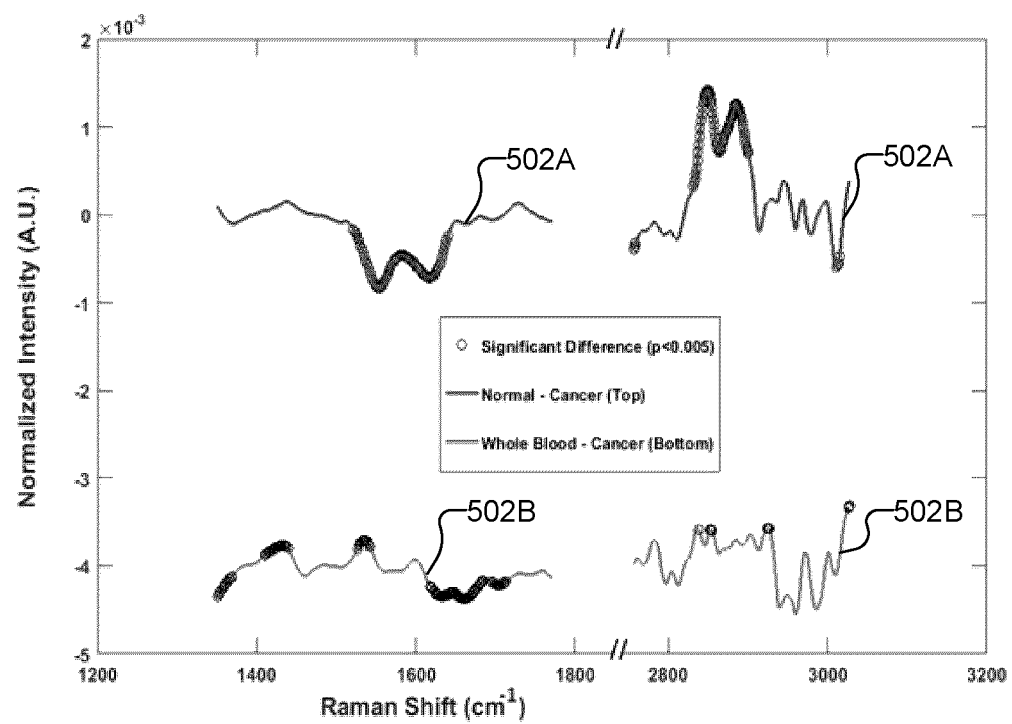
FIG. 8 is a graph of Raman difference spectra calculated from the Raman spectra of FIG. 7 and superimposed with data obtained from Mann-Whitney U (MWU) calculations.

FIG. 8 is a plot of Mann-Whitney U (MWU) statistics superimposed on the difference spectra for two subtractions: Normal-Cancer (curves 502A) and Whole Blood-Cancer (curves 502B). The MWU statistics were calculated to determine if the normal and cancerous spectra illustrated in FIG. 7 were in fact significantly different. Locations with circles show wavenumbers where there are significant differences between the two groups (p-values≤0.005).

In the high frequency region (2800-3050 $cm^{-1}$), there are significant changes in both data sets (curves 502A and curves 502B) around the 2887 $cm^{-1}$ lipid peak. This suggests that lipid changes occur during pathology progression. In the low frequency region (1350-1800 $cm^{-1}$) there are significant changes between 1600 and 1700 $cm^{-1}$ in the whole blood-cancer data set (curves 502B), suggesting that differences due to the presence of the 1659 $cm^{-1}$ amide I band are detectable.

Significant changes in both data sets (curves 502A and curves 502B) were also found at the 1550 $cm^{-1}$ and 1615 $cm^{-1}$ bands. These suggest protein differences between pathologies that are not attributed to the increased presence of blood in cancer tissue.

Interpretation of Terms

Unless the context clearly requires otherwise, throughout the description and the claims:

"comprise", "comprising", and the like are to be construed in an inclusive sense, as opposed to an exclusive or exhaustive sense; that is to say, in the sense of "including, but not limited to";

"connected", "coupled", or any variant thereof, means any connection or coupling, either direct or indirect, between two or more elements; the coupling or connection between the elements can be physical, logical, or a combination thereof;

"herein", "above", "below", and words of similar import, when used to describe this specification, shall refer to this specification as a whole, and not to any particular portions of this specification;

"or", in reference to a list of two or more items, covers all of the following interpretations of the word: any of the items in the list, all of the items in the list, and any combination of the items in the list;

"approximately" means a slight variation from the specified value, preferably within plus or minus 5 percent of the specified value unless otherwise specified;

"about" means a slight variation from the specified value, preferably within plus or minus 10 percent of the specified value unless otherwise specified;

the singular forms "a", "an", and "the" also include the meaning of any appropriate plural forms.

Words that indicate directions such as "vertical", "transverse", "horizontal", "upward", "downward", "forward", "backward", "inward", "outward", "vertical", "transverse", "left", "right", "front", "back", "top", "bottom", "below", "above", "under", and the like, used in this description and any accompanying claims (where present), depend on the specific orientation of the apparatus described and illustrated. The subject matter described herein may assume various alternative orientations. Accordingly, these directional terms are not strictly defined and should not be interpreted narrowly.

While processes or blocks are presented in a given order, alternative examples may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed in parallel, or may be performed at different times.

In addition, while elements are at times shown as being performed sequentially, they may instead be performed simultaneously or in different sequences. It is therefore intended that the following claims are interpreted to include all such variations as are within their intended scope.

Where a component (e.g. a software module, processor, filter, assembly, device, circuit, etc.) is referred to above, unless otherwise indicated, reference to that component (including a reference to a "means") should be interpreted as including as equivalents of that component any component which performs the function of the described component (i.e., that is functionally equivalent), including components which are not structurally equivalent to the disclosed structure which performs the function in the illustrated exemplary embodiments of the invention.

Specific examples of systems, methods and apparatus have been described herein for purposes of illustration. These are only examples. The technology provided herein can be applied to systems other than the example systems described above. Many alterations, modifications, additions, omissions, and permutations are possible within the practice of this invention. This invention includes variations on described embodiments that would be apparent to the skilled addressee, including variations obtained by: replacing features, elements and/or acts with equivalent features, elements and/or acts; mixing and matching of features, elements and/or acts from different embodiments; combining features, elements and/or acts from embodiments as described herein with features, elements and/or acts of other technology; and/or omitting combining features, elements and/or acts from described embodiments.

Various features are described herein as being present in "some embodiments". Such features are not mandatory and may not be present in all embodiments. Embodiments of the invention may include zero, any one or any combination of two or more of such features. This is limited only to the extent that certain ones of such features are incompatible with other ones of such features in the sense that it would be impossible for a person of ordinary skill in the art to construct a practical embodiment that combines such incompatible features. Consequently, the description that "some embodiments" possess feature A and "some embodiments" possess feature B should be interpreted as an express indication that the inventors also contemplate embodiments which combine features A and B (unless the description states otherwise or features A and B are fundamentally incompatible).

It is therefore intended that the following appended claims and claims hereafter introduced are interpreted to include all such modifications, permutations, additions, omissions, and sub-combinations as may reasonably be inferred. The scope of the claims should not be limited by the preferred embodiments set forth in the examples, but should be given the broadest interpretation consistent with the description as a whole.

What is claimed is:

1. An endoscope comprising:
at least one excitation optical fiber having a coupling at a proximal end thereof for connecting the at least one excitation optical fiber to an output of a light source the at least one excitation optical fiber having a diameter in a range of about 100 to 200 µm;
a plurality of collection optical fibers extending to a coupling at a proximal end thereof for connecting the collection optical fibers to an input of a spectrograph each of the collection optical fibers having a diameter in a range of approximately 50 to 200 µm; a sheath comprising a bore enclosing distal ends of the at least one excitation optical fiber and the plurality of collection optical fibers from a probe tip at the distal ends of the at least one excitation optical fiber and the collection optical fibers for a distance of at least 30 cm but not more than 135 cm along the excitation and collection optical fibers, the sheath comprising a tube of a heat shrink FEP material having an outer diameter of not more than 1.35 mm the sheath and contained excitation and collection optical fibers bendable with a bend radius of 20 mm or less while maintaining a light transmissivity along the at least one excitation optical fiber and the plurality of collection optical fibers of not less than 90% of a light transmissivity when the sheath and contained excitation and collection optical fibers are straight;
the probe tip comprising a cured adhesive bonded to end portions of the excitation and collection optical fibers and to a chemically etched end portion of the sheath, the cured adhesive bonded to the excitation and collection optical fibers over a distance not exceeding 5 mm from ends of the excitation and collection optical fibers, the distal end of the probe tip being polished and exposing the ends of the excitation and collection optical fibers;
wherein a distal end of the at least one excitation optical fiber is centered in the probe tip and the distal ends of the collection optical fibers are arranged symmetrically around the distal end of the at least one excitation optical fiber in a plurality of rings;
wherein, within the sheath, the excitation and collection optical fibers are free to move longitudinally relative to one another and to an inner wall of the sheath in response to bending of the endoscope.

2. The endoscope of claim 1 wherein each of the at least one excitation optical fiber and the collection optical fibers have a numerical aperture of 0.22.

3. The endoscope of claim 1 wherein the at least one excitation optical fiber is encased in an opaque jacket.

4. The endoscope of claim 3 wherein the opaque jacket comprises a tubular stainless steel jacket.

5. The endoscope of claim 1 wherein the collection optical fibers are encased in opaque jackets.

6. The endoscope of claim 5 wherein the opaque jackets comprise stainless steel jackets.

7. The endoscope of claim 1 wherein the at least one excitation optical fiber has an aluminum coating.

8. The endoscope of claim 1 wherein the at least one excitation optical fiber or at least one of the collection optical fibers comprise hydroxyl silica optical fibers.

9. The endoscope of claim 1 wherein the outer diameter of the sheath is 0.5 mm to 1.35 mm.

10. The endoscope of claim 1 wherein the sheath has a wall thickness of 0.2 mm to 1 mm.

11. The endoscope of claim 1 wherein the sheath has a coefficient of friction of 0.04 to 0.06.

12. The endoscope of claim 1 wherein the chemically etched end portion of the sheath comprises a carbonaceous layer.

13. The endoscope of claim 1 wherein the sheath has a length of 130 cm.

14. The endoscope of claim 1 wherein the sheath comprises a flexible portion.

15. The endoscope of claim 1 wherein the sheath comprises a layer of coating sealing a first end of the sheath to the proximal end of at least one of the at least one excitation optical fiber or at least one of the collection optical fibers.

* * * * *